United States Patent
Hinrichs et al.

(10) Patent No.: US 7,994,370 B2
(45) Date of Patent: Aug. 9, 2011

(54) METHOD FOR DEPLETION OF SULFUR AND/OR COMPOUNDS CONTAINING SULFUR FROM A BIOCHEMICALLY PRODUCED ORGANIC COMPOUND

(75) Inventors: Matthias Hinrichs, Ludwigshafen (DE); Heiko Urtel, Bobenheim-Roxheim (DE); Jochen Steiner, Bensheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/570,170

(22) Filed: Sep. 30, 2009

(65) Prior Publication Data

US 2010/0087689 A1 Apr. 8, 2010

(30) Foreign Application Priority Data

Oct. 2, 2008 (EP) .................................... 08165727

(51) Int. Cl.
*C07C 29/76* (2006.01)
(52) U.S. Cl. ....................................................... 568/917
(58) Field of Classification Search ................... 568/917
See application file for complete search history.

(56) References Cited

U.S. PATENT DOCUMENTS

| 5,254,467 A | 10/1993 | Kretschmann et al. |
| 6,514,733 B1 | 2/2003 | Emptage et al. |
| 6,531,052 B1 | 3/2003 | Frye et al. |
| 2003/0070966 A1 | 4/2003 | Khare |
| 2003/0113598 A1 | 6/2003 | Chow et al. |
| 2007/0167530 A1 | 7/2007 | Gerlach et al. |
| 2010/0233054 A1 | 9/2010 | Steiner et al. |

FOREIGN PATENT DOCUMENTS

| DE | 3829618 A1 | 3/1990 |
| JP | 2911961 B2 | 4/1999 |
| WO | WO-03/020850 A2 | 3/2003 |
| WO | WO-2005/063354 A1 | 7/2005 |
| WO | WO-2007/117481 A2 | 10/2007 |
| WO | WO-2009/019238 A1 | 2/2009 |
| WO | WO-2010/023249 A1 | 3/2010 |

*Primary Examiner* — Sikarl A Witherspoon
(74) *Attorney, Agent, or Firm* — Connolly Bove Lodge & Hutz LLP

(57) ABSTRACT

Method of reducing the concentration of sulfur and/or a sulfur-containing compound in a biochemically prepared organic compound by bringing the respective organic compound into contact with an adsorbent, wherein the adsorbent is a clay doped with silver and/or a silver compound.

24 Claims, No Drawings

METHOD FOR DEPLETION OF SULFUR AND/OR COMPOUNDS CONTAINING SULFUR FROM A BIOCHEMICALLY PRODUCED ORGANIC COMPOUND

RELATED APPLICATIONS

This application claims benefit of European Application No. 08165727.2, filed Oct. 2, 2008.

The present invention relates to a method of reducing the concentration of sulfur and/or sulfur-containing compounds in a biochemically prepared organic compound, which comprises bringing the respective organic compound into contact with an adsorbent.

There is an increasing demand for biochemically prepared chemical compounds, e.g. compounds prepared by fermentation, as, for example, building blocks in the chemical synthesis of high-value chemicals or as "green" fuels.

(Cf., for example, H. van Bekkum et al., Chem. for Sustainable Development 11, 2003, pages 11-21).

Examples of these renewable resources are alcohols such as ethanol, butanol and methanol, diols such as 1,3-propanediol and 1,4-butanediol, triols such as glycerol, carboxylic acids such as lactic acid, acetic acid, propionic acid, citric acid, butyric acid, formic acid, malonic acid and succinic acid.

In place of synthetic ethanol, which is produced predominantly by hydration of ethylene, ethanol from biological sources, known as bioethanol, can also be used for many applications.

Instead of synthetic 1,3-propanediol, which is predominantly prepared by hydrolysis of acrolein to 3-hydroxypropanal in the presence of an acid catalyst followed by metal-catalyzed hydrogenation or by hydroformylation of ethylene oxide (Industrial Organic Chemistry, Weissermel and Arpe, 2003), 1,3-propanediol from biological sources, known as bio-1,3-propanediol, can also be used for many applications (U.S. Pat. No. 6,514,733 A, DE 38 29 618 A).

Instead of synthetic lactic acid prepared by hydrolysis of lactonitrile, lactic acid from biological sources can also be used for many applications (K. Weissermel and H.-J. Arpe, Industrial Organic Chemistry, Wiley-VCH, Weinheim, 2003, p. 306).

Edible oils and animal fats can be transesterified to produce biodiesel. In addition to biodiesel, a glycerol fraction is formed in this process. Uses of glycerol comprise applications in the chemical industry, for instance the preparation of pharmaceuticals, cosmetics, polyether isocyanates, glycerol tripolyethers (K. Weissermel and H,-J. Arpe, Industrial Organic Chemistry, Wiley-VCH, Weinheim, 2003, p. 303).

Uses of ethanol comprise applications in the chemical industry, for instance the preparation of ethylamines, the preparation of ethyl esters from carboxylic acids (in particular ethyl acetate), the preparation of butadiene or ethylene, the preparation of ethyl acetate via acetaldehyde and the preparation of ethyl chloride (K. Weissermel and H.-J. Arpe, Industrial Organic Chemistry, Wiley-VCH, Weinheim, 2003), and in the cosmetics and pharmaceuticals industry or in the food industry and also in cleaners, solvents and paints (N. Schmitz, Bioethanol in Deutschland, Landwirtschaftsverlag, Münster, 2003).

Further uses are: feed in steam reforming processes and hydrogen source in fuel cells (S. Velu et al., Cat. Letters 82, 2002, pages 145-52; A. N. Fatsikostas et al., Cat. Today 75, 2002, pages 145-55; F. Aupretre et al., Cat. Commun. 3, 2002, pages 263-67; V. Fierro et al., Green Chem. 5, 2003, pages 20-24; M. Wang, J. of Power Sources 112, 2002, pages 307-321).

Uses of 1,3-propanediol comprise applications in the chemical industry, for instance the production of pharmaceuticals, polyesters, polytrimethylene terephthalates, fibers.

Uses of lactic acid are in the food industry and in the production of biodegradable polymers.

The use of biochemically prepared compounds such as bioethanol, bio-1,3-propanediol or lactic acid, especially in particularly pure form, would be more advantageous and cheaper in many of these applications.

The purification or isolation of the biochemically prepared compounds is frequently carried out by distillation in complicated, multistage processes.

However, the advantage of the respective biochemically prepared compound is, as has been recognized according to the invention, frequently decreased by the compound comprising small amounts of sulfur and/or sulfur-containing compounds, in particular specific sulfur compounds, even after the known purification processes and the sulfur or the sulfur-containing compounds frequently interfering in the respective application(s).

Thus, the sulfur content of bioethanol interferes in its use in ammination to form ethylamines by poisoning the metal catalyst. A similar situation applies in amminations of other bioalcohols.

The ammination of alcohols is carried out industrially over hydrogenation/dehydrogenation catalysts, in particular heterogeneous hydrogenation/dehydrogenation catalysts, by reaction of the respective alcohol with ammonia, primary or secondary amines at elevated pressure and elevated temperature in the presence of hydrogen. C.f., for example, Ullmann's Encyclopedia of Industrial Chemistry, sixth edition, 2000, 'Aliphatic Amines: Production from alcohols'.

The catalysts usually comprise transition metals, for instance metals of groups VIII and IB, often copper, as catalytically active components which are frequently applied to an inorganic support such as aluminum oxide, silicon dioxide, titanium dioxide, carbon, zirconium oxide, zeolites, hydrotalcites and similar materials known to those skilled in the art.

If the corresponding bioalcohol is used, the catalytically active metal surface of the heterogeneous catalysts becomes coated with the sulfur or sulfur compounds introduced via the bioalcohol to an increasing extent over time. This leads to accelerated catalyst deactivation and thus to a significant deterioration in the economics of the respective process.

The sulfur content of bioethanol also has an adverse effect due to poisoning of the catalyst, e.g. in steam reforming processes for the production of hydrogen and in fuel cells.

In general, the sulfur content of chemicals derived from natural raw materials will have an adverse effect on a reaction carried out using them, for instance as a result of, as described, metal centers being sulfurized and thereby deactivated, or acidic or basic centers being occupied, secondary reactions occurring or being catalyzed, formation of deposits in production plants and contamination of the products.

A further adverse effect of sulfur and/or sulfur-containing compounds in the biochemically prepared compounds is their typical unpleasant odor which is disadvantageous, in particular, in cosmetic applications, in disinfectants, in foodstuffs and in pharmaceutical products.

It is therefore of great economic interest to reduce the concentration of sulfur and/or sulfur-containing compounds in biochemically prepared organic compounds such as bioethanol, bio-1,3-propanediol, bio-1,4-butanediol, bio-1-butanol (in general: bioalcohols), or to remove the sulfur and/or the sulfur-containing compounds virtually entirely, by means of a desulfurization step preceding their use.

WO 2003 020850 A, US 2003 070966 A1, US 2003 113598 A1 and U.S. Pat. No. 6,531,052 B1 concern the removal of sulfur from liquid hydrocarbons (petroleum spirit). Chemical Abstracts No. 102: 222463 (M. Kh. Annagiev et al., Doklady—Akademiya Nauk Azerbaidzhanskoi SSR, 1984, 40 (12), 53-6) describes decreasing the concentration of S compounds in technical-grade ethanol (not bioethanol) from 25-30 to 8-17 mg/l by bringing the ethanol into contact with zeolites of the clinoptilolite and mordenite types at room temperature, with the zeolites having been conditioned beforehand at 380° C. for 6 hours and in some cases treated with metal salts, in particular $Fe_2O_3$. The S compounds removed are $H_2S$ and alkyl thiols (R—SH).

WO 2007/117481 A2 (Archer-Daniels-Midland Comp.) describes the reduction or removal of sulfur compounds from an alcohol stream using adsorbents such as anion exchangers, alumina, aluminosilicate, activated carbon, barium salts and clay (paragraph 0006, page 2) or metals such as iron, copper, zinc, bronze (paragraph 0050, page 11; Example 6, page 15; claim 1, page 17).

WO 2005/063354 A1 (BASF AG) relates to a method of reducing the concentration of sulfur and/or a sulfur-comprising compound in a biochemically prepared organic compound, which comprises bringing the respective organic compound into contact with an adsorbent. The adsorbent is, in particular, a specific zeolite.

JP 2911961 B2 (Nikki Kabushiki Kaisha) describes a method of purifying an aqueous alcohol, in which dimethyl disulfide and mercaptan are adsorbed by means of adsorbents comprising silver or silver oxide and aluminum oxide. The document teaches that dimethyl sulfoxide (DMSO) and dimethyl sulfide (DMS) are not adsorbed by this method.

It was an object of the present invention to discover an improved economical method of treating biochemically prepared organic compounds such as bioalcohols, e.g. bioethanol, by means of which the corresponding treated compound is obtained in high yield, space-time yield and selectivity and which when used, for example, in chemical synthetic processes such as the preparation of ethylamines, in particular monoethylamine, diethylamine and triethylamine, from bioethanol, and also in other applications, e.g. in the chemical, cosmetic or pharmaceutical industry or in the food industry, has improved properties.

In particular, the use of a treated bioethanol should make increased catalyst operating fifes in the synthesis of ethylamines possible.

(Space-time yields are reported in 'amount of product/(adsorbent volume·time)' (kg/($l_{adsorbent}$·h)) and/or 'amount of product/(reactor volume·time)' (kg/($l_{reactor}$·h)).

We have accordingly found a method of reducing the concentration of sulfur and/or a sulfur-containing compound in a biochemically prepared organic compound, which comprises bringing the respective organic compound into contact with an adsorbent, wherein the adsorbent is a clay doped with silver and/or a silver compound.

Furthermore, the advantageous use of ethanol which has been obtained by the method according to the invention as solvent, disinfectant, as component in pharmaceutical or cosmetic products or in foodstuffs or in cleaners, as feed in steam reforming processes for the synthesis of hydrogen or in fuel cells as component in fuels for the operation of internal combustion engines or as building block in chemical synthesis has been found.

The method of the invention is particularly useful for reducing the concentration of sulfur or a sulfur-containing compound in a compound prepared by fermentation.

The sulfur-containing compounds are inorganic or organic compounds, in particular symmetrical or unsymmetrical $C_{2-10}$-dialkyl sulfides, particularly $C_{2-6}$-dialkyl sulfides such as diethyl sulfide, di-n-propyl sulfide, diisopropyl sulfide, very particularly dimethyl sulfide, symmetrical or unsymmetrical $C_{2-10}$-dialkyl disulfides, particularly $C_{2-6}$-dialkyl disulfides such as dimethyl disulfide, symmetrical or unsymmetrical $C_{2-10}$-dialkyl sulfoxides such as dimethyl sulfoxide, diethyl sulfoxide, dipropyl sulfoxide, $C_{1-10}$-alkyl mercaptans such as methyl mercaptan, ethyl mercaptan, n-propyl mercaptan, 3-methylthio-1-propanol and/or S-containing amino acids such as methionine and S-methylmethionine.

The biochemically prepared organic compound is preferably an alcohol, ether or a carboxylic acid, in particular methanol, ethanol, 1,3-propanediol, 1,4-butanediol, 1-butanol, glycerol, tetrahydrofuran, furfural, lactic acid, succinic acid, malonic acid, citric acid, acetic acid, propionic acid, 3-hydroxypropionic acid, butyric acid, formic acid or gluconic acid.

The alcohol is preferably a $C_{1-5}$-alcohol having a boiling point $\leq 290°$ C./1 bar (absolute pressure).

The clay as adsorbent is preferably a mineral from the serpentine-kaolin, talc-pyrophyllite, smectite, vermiculite, illite, mica, brittle mica, chlorite or sepiolite-palygorskite group or a mixture of two or more minerals from these groups.

The clay as adsorbent is particularly preferably a mineral from the serpentine-kaolin or talc-pyrophyllite group or a mixture of two or more minerals from these groups.

The clay particularly preferably comprises a kaolinite, illite, illenite, pyrophyllite, celadonite, beidellite, nontronite, hectorite, saponite, vermiculite, clinochlore, sheridanite, sudoite, cookeite, danobassite, rectorite, tosudite, corrensite, sepiolite, loughlinite, palygorskite, montmorillonite, bentonite, smectite, chlorite, glauconite, muscovite, vermiculite, talc or a mixture of two or more of these minerals as clay mineral.

Clays comprising montmorillonite, bentonite, smectite, talc, kaolinite, Mite, chlorite, pyrophyllite and/or vermiculite are preferably used for producing the adsorbent.

Very particular preference is given to using clays comprising montmorillonite, bentonite and/or kaolinite for producing the adsorbent.

The abovementioned clays, including commercial clays, are described, for example, in K, Jasmund/G. Lagaly (Editors), Tonminerale und Tone—Struktur, Eigenschaften, Anwendung and Einsatz in Industrie und Umwelt, Steinkopff Verlag Darmstadt, 1983.

The adsorbent is doped with silver [elemental silver, silver (0)] and/or a silver compound. Preference is given to doping with a silver compound.

This doping can be effected, for example, by impregnating the clay, preferably as shaped body, with an impregnation solution comprising an Ag(I) salt, mixing the clay powder with a solid Ag(I) compound or elemental silver or mixing the clay powder with an aqueous solution comprising an Ag(I) salt. The silver compound is preferably applied to the clay by mixing the clay powder with an aqueous solution comprising an Ag(I) salt.

Methods of producing such doped clays are known to those skilled in the art. Methods analogous to known impregnations of solids, e.g. impregnations or compounding of aluminum oxide can be employed.

To produce the silver-doped adsorbent, the adsorbent doped with a silver compound can be treated by methods known to those skilled in the art with a reducing agent, in particular hydrogen.

The clay is preferably doped with such an amount of silver and/or silver compound that a content in the range from 0.1 to 20% by weight, particularly preferably from 0.5 to 15% by weight, very particularly preferably from 1 to 10% by weight, more preferably from 4 to 9% by weight, in each case calculated as Ag, is obtained.

The silver compound is preferably a silver(I) compound, especially a silver(I) salt.

In particular, the silver compound is silver oxide ($Ag_2O$), silver carbonate ($Ag_2CO_3$), silver nitrate ($AgNO_3$), silver sulfate ($Ag_2SO_4$), a silver halide (AgI, AgBr, AgCl, AgF) or silver sulfide ($Ag_2S$).

If the adsorbent is produced as shaped bodies, for instance for a fixed-bed process according to the invention, it can be used in any desired shape. Typical shaped bodies are spheres, extrudates, hollow extrudates, star extrudates, pellets, crushed material, etc., having characteristic diameters of from 0.5 to 5 mm, or monolites and similar structured packing elements (cf. Ullmann's Encyclopedia, sixth edition, 2000 Electronic Release, Chapter Fixed-Bed Reactors, Par. 2: Catalyst Forms for Fixed-Bed Reactors).

In the case of a suspension procedure, the adsorbent is used in powder form. The filtration in the suspension processes according to the invention can be carried out batchwise, for instance by deep bed filtration. In continuous processes, crossflow filtration, for example, is a possibility.

To carry out the method of the invention, the doped alumina is preferably brought into contact with the organic compound at a temperature in the range from 10° C. to 200° C., in particular from 15° C. to 50° C., more particularly from 18° C. to 30° C.

The contacting of the organic compound with the doped alumina is preferably carried out at an absolute pressure in the range from 1 to 200 bar, in particular from 1 to 10 bar, more particularly from 1 to 3 bar.

It is particularly preferably carried out at room temperature and under atmospheric pressure.

In a preferred embodiment of the method of the invention, the respective organic compound is brought into contact with the doped alumina in the liquid phase, i.e. in liquid form or dissolved or suspended in a solvent or diluent.

Possible solvents are, in particular, those which are able to dissolve the compounds to be purified virtually completely or are completely miscible with these and are inert under the process conditions.

Examples of suitable solvents are water, cyclic and alicyclic ethers, e.g. tetrahydrofuran, dioxane, methyl tert-butyl ether, dimethoxyethane, dimethoxypropane, dimethyl diethylene glycol, aliphatic alcohols such as methanol, ethanol, n-propanol or isopropanol, n-butanol, 2-butanol, isobutanol or tert-butanol, carboxylic esters such as methyl acetate, ethyl acetate, propyl acetate or butyl acetate, and also aliphatic ether alcohols such as methoxypropanol.

The concentration of the compound to be purified in the liquid, solvent-containing phase can in principle be chosen freely and is frequently in the range from 20 to 95% by weight, based on the total weight of the solution/mixture.

In the method of the invention, the biochemically prepared compound preferably comprises from 0 to 50% by weight, particularly preferably from 0.5 to 10% by weight, very particularly preferably from 1 to 5% by weight, of water ($H_2O$).

The method of the invention is preferably carried out in the absence of hydrogen.

The method of the invention can be carried out in the gas or liquid phase, in the fixed-bed or suspension mode, with or without backmixing, continuously or batchwise according to the methods known to those skilled in the art (e.g. as described in Ullmann's Encyclopedia, sixth edition, 2000 electronic release, Chapter "Adsorption"). A continuous method is preferred.

To obtain a very high reduction in the concentration of sulfur and/or the sulfur-comprising compound, processes having a low degree of backmixing are particularly preferred.

The contacting of the organic compound with the doped clay is preferably carried out at a space velocity in the range from 0.1 to 5 $kg_{organic\ compound}/(l_{adsorbent} \cdot h)$, in particular in the range from 0.3 to 2.5 $kg_{organic\ compound}/(l_{adsorbent} \cdot h)$ [i.e. kg of organic compound per liter of adsorbent (bulk volume) and hour].

The method of the invention makes it possible, in particular, to reduce the concentration of sulfur and/or sulfur-containing compounds in the respective organic compound by $\geq 90\%$ by weight, particularly preferably $\geq 95\%$ by weight, very particularly preferably $\geq 98\%$ by weight (in each case calculated as S).

The method of the invention makes it possible, in particular, to reduce the concentration of sulfur and/or sulfur-comprising compounds in the respective organic compound to a residual content of <2 ppm by weight, particularly preferably <1 ppm by weight, very particularly preferably from 0 to <0.1 ppm by weight (in each case calculated as S), for example determined by the Wickbold method (DIN EN 41).

The bioethanol which is preferably used in the method of the invention preferably comprises a denaturant such as cyclohexane, methyl ethyl ketone (MEK), petroleum ether or diethyl phthalate.

The bioethanol which is preferably used in the method of the invention is generally produced from agricultural products such as molasses, cane sugar juice, maize starch or from products of wood saccharification and from sulfite waste liquors by fermentation.

Preference is given to using bioethanol which has been obtained by fermentation of glucose with elimination of $CO_2$ (K. Weissermel and H.-J. Arpe, Industrial Organic Chemistry, Wiley-VCH, Weinheim, 2003, p. 194; Electronic Version of Sixth Edition of Ullmann's Encyclopedia of Industrial Chemistry, 2000, Chapter Ethanol, Paragraph Fermentation). The ethanol is in particular isolated from the fermentation broths by distillation methods: Electronic Version of Sixth Edition of Ullmann's Encyclopedia of Industrial Chemistry, 2000, Chapter Ethanol, Paragraph Recovery and Purification.

According to the invention, the ethanol prepared using the method found is advantageously used as building block in chemical synthesis, e.g.

in processes (known to those skilled in the art) for preparing a primary, secondary or tertiary ethylamine, a monoethylamine or diethylamine, in particular monoethylamine, diethylamine and/or triethylamine, by reacting the ethanol with $NH_3$, a primary amine or a secondary amine in the presence of hydrogen at elevated temperatures and pressures in the presence of a heterogeneous catalyst comprising one or more metal(s) of group VIII and/or IB of the Periodic Table, in processes (known to those skilled in the art) for preparing an ethyl ester, in particular by esterification of ethanol with a carboxylic acid or transesterification of a carboxylic ester with ethanol, in processes (known to those skilled in the art) for preparing ethylene by dehydration, as solvent, disinfectant, and as component in pharmaceutical or cosmetic products or in foodstuffs or in cleaners, as feed in steam reforming processes for the synthesis of hydrogen or in fuel cells as component in fuels for the operation of internal combustion engines.

EXAMPLES

All ppm figures in this document are by weight.
Production of the adsorbents:

Example 1

Comparison 300 g of clay powder (K10 powder from Süd-Chemie AG, based predominantly on montmorillonite) were placed in a kneader, deionized water was added a little at a time while kneading until an extrudable kneaded composition was obtained.

The kneaded composition was converted into 1.5 mm extrudates.

Water addition: 195 ml, kneading time: 10 min, pressing pressure: 75 bar.

The extrudates formed were dried at 120° C. in a convection drying oven for 16 h and subsequently calcined at 450° C. in a furnace for 2 hours.

Example 2

According to the Invention

Kneading of clay powder with 7% by weight of Ag(I) from $Ag_2O$:

The clay powder (162.7 g; the same as for Example 1) was placed in a kneader, the Ag oxide (12.25 g) in powder form was introduced into the kneader and this mixture was kneaded with addition of water (115 ml) over 10 minutes to give an extrudable composition.

The composition formed was subsequently extruded to give 1.5 mm extrudates [pressure (extruder): 85 bar] and the resulting extrudates were dried at 120° C. in a convection drying oven for 16 hours.

Weight obtained: 128.98 g

Example 3

Comparison

Production of an Ag Doped Zeolite Using $AgNO_3$ as Described in WO 2005/063354 A1 (BASF AG)

65 g of the zeolite (molecular sieve 13× spheres from Zeochem AG—Zeochem®Z10-02—1.6-2.5 mm diameter, Na form) were placed in a bottle, 400 ml of water were added. An Ag nitrate solution (9.86 g of $AgNO_3$ dissolved in $H_2O$ and made up to 100 ml) was added to this mixture over a period of 1 hour while shaking continuously (shaking machine 120 Skt.). The mixture was subsequently shaken overnight for 23 hours, and then washed free of nitrate using 12 l of $H_2O$. The resulting spheres were dried at 120° C. in a convection drying oven for 16 hours.

| Weight obtained: | 59.04 g |
| --- | --- |
| Ag(I) content: | 6.3% by weight |

Example 4

Comparison

Production of an Ag Doped Zeolite Using $AgNO_3$ as Described in WO 2005/063354 A1 (BASF AG)

65 g of the zeolite (molecular sieve 13× spheres from Zeochem AG—Zeochem® Z10-02—1.6-2.5 mm diameter, Na form) were placed in a bottle, 400 ml of water were added. An Ag nitrate solution (22.4 g of $AgNO_3$ dissolved in $H_2O$ and made up to 100 ml) was added to this mixture over a period of 1 hour while shaking continuously (shaking machine 120 Skt.). The mixture was subsequently shaken overnight for 23 hours, and then washed free of nitrate using 14 l of $H_2O$. The resulting spheres were dried at 120° C. in a convection drying oven for 16 hours.

| Weight obtained: | 66.28 g |
| --- | --- |
| Ag(I) content: | 15.6% by weight |

Example 5

Comparison

Production of an Ag-Doped Zeolite Using $AgNO_3$ as Described in WO 2005/063354 A1 (BASF AG)

The $AgNO_3$ (7.71 g) was dissolved in water and made up to a total volume of 300 ml. The zeolite ZSM-5 (from Zeochem AG: ZEOcat® PZ-2/40 Na form, 200 g) was then slowly added to the Ag nitrate solution while stirring. The mixture was subsequently stirred at room temperature for 2 hours, then filtered and washed free of nitrate. The powder was dried at 120° C. in a convection drying oven for 16 hours.

| Weight obtained: | 155.83 g |
| --- | --- |

To convert the powder into extrudates, 4.67 g of Walocel together with the dried powder were placed in a kneader and processed with 155 ml of water for 30 minutes to form an extrudable composition. The composition was then extruded to give 1.5 mm extrudates (pressing pressure: 55 bar). The extrudates were dried at 120° C. for 16 hours.

| Weight obtained: | 79.04 g |
| --- | --- |
| Ag(I) content: | 1.8% by weight |

Example 6

Comparison

Production of an Ag-Doped Zeolite Using $AgNO_3$ as Described in WO 2005/063354 A1 (BASF AG)

The $AgNO_3$ (27.7 g) was dissolved in water and made up to a total volume of 300 ml. The zeolite ZSM-5 (from Zeochem AG: ZEOcat® PZ-2/40 Na form, 200 g) was then slowly added to the Ag nitrate solution while stirring. The mixture was subsequently stirred at room temperature for 2 hours, then filtered and washed free of nitrate. The powder was dried at 120° C. in a convection drying oven for 16 hours.

| Weight obtained: | 171.19 g |
|---|---|

To convert the powder into extrudates, 5.14 g of Walocel together with the dried powder were placed in a kneader and processed with 165 ml of water for 30 minutes to form an extrudable composition. The composition was then extruded to give 1.5 mm extrudates (pressing pressure: 70 bar). The extrudates were dried at 120° C. for 16 hours.

| Weight obtained: | 113.25 g |
|---|---|
| Ag(I) content: | 3.3% by weight |

Use of the adsorbents from Examples 1 to 6 for reducing the concentration of sulfur and/or a sulfur-comprising compound in bioethanol:

The desulfurization experiments were all carried out in the same way:

40 ml of the respective adsorbent produced in the examples were introduced into a reactor (diameter: 16 mm). A temperature sensor (diameter: 3.17 mm) was installed in this reactor. All experiments were carried out at room temperature. The amount of ethanol was selected so that a whsv (weight hourly space velocity) of 0.625 $kg_{ethanol}/(l_{adsorbent} \cdot h)$ was achieved. The ethanol was passed over the adsorbent from the top downward by means of a pump. The experiments were carried out without application of pressure, i.e. at ambient pressure.

Various sulfur components were added to the ethanol (for type and amount of the sulfur components, see the following table). The experiments were carried out in a single pass without recycle. A GC analysis was carried out on the discharge from the reactor at regular intervals and the sulfur components were measured. This enabled the operating life of the adsorbent and the time (h) for which this takes up all of the sulfur or sulfur-comprising compound to be determined. The components which have then broken through in each case are indicated in the following table.

The results are shown in the following table:

It can be seen that the adsorbent based on Ag(I)/clay (Example 2) has significantly better uptake properties (both in terms of amount and in terms of sulfur components) than any other adsorbent in the examples at comparable amounts of sulfur in the ethanol.

Even the adsorbent in Example 3, which has a similar Ag content to the clay adsorbent in Example 2, is not able to desulfurize the ethanol completely under these conditions. This demonstrates the superiority of the clay system over zeolite or $Al_2O_3/SiO_2$ systems. Even the high silver loading of the adsorbent in Example 4 is not sufficient to achieve the desulfurization performance of the clay adsorbent from Example 2. Examples 5 and 6 demonstrate that adjustment of the adsorbent known from the literature (Example 5) is only able to remove less sulfur. An attempt to load this adsorbent with as much Ag(I) as possible in order to improve its desulfurization properties resulted in Example 6. More than 3.3% by weight of Ag(I) could not be applied although arithmetically far more Ag should have remained on the support. However, an increase in the amount of Ag from 1.8 to 3.3% by weight led to no significant changes in the properties.

The invention claimed is:

1. A method of reducing the concentration of sulfur and/or a sulfur-containing compound in a biochemically prepared organic compound, which comprises bringing the respective organic compound into contact with an adsorbent, wherein the adsorbent is a clay doped with silver and/or a silver compound.

2. The method according to claim 1 for reducing the concentration of sulfur and/or a sulfur-containing compound in a compound prepared by fermentation.

3. The method according to claim 1 for reducing the concentration of $C_{2-10}$-dialkyl sulfides, $C_{2-10}$-dialkyl disulfides, $C_{2-10}$-dialkyl sulfoxides, $C_{2-10}$-alkyl mercaptans, 3-methylthio-1-propanol and/or S-containing amino acids.

4. The method according to claim 1 for reducing the concentration of dimethyl sulfide, dimethyl disulfide and/or n-propyl mercaptan.

5. The method according to claim 1, wherein the biochemically prepared organic compound is an alcohol, ether or a carboxylic acid.

| Example | Adsorbent | Ag(I) content [% by weight] | Time until breakthrough [h] | S component introduced | Total sulfur concentration at inlet [ppm] | S component which has broken through | Amount of S in gram which has been taken up up to this point, calculated as S $[g_s/l_{(adsorbent)}]$ |
|---|---|---|---|---|---|---|---|
| 1 | Pure clay (comparison) | 0 | 0 | DMS | 14.05 | DMS | 0.00 |
| 2 | Doped clay | 6.6 | 324 | DMS, DMDS, PrSH | 15.50 | DMS, DMDS, PrSH | 2.94 |
| 3 | Molecular sieve 13X (comparison) | 6.3 | 0 | DMS, DMDS, PrSH | 15.83 | DMS, PrSH | 0.00 |
| 4 | Molecular sieve 13X (comparison) | 15.6 | 31 | DMS DMDS, PrSH | 15.57 | DMS | 0.31 |
| 5 | ZSM-5 (comparison) | 1.8 | 20 | DMS DMDS, PrSH | 22.71 | DMDS | 0.29 |
| 6 | ZSM-5 (comparison) | 3.3 | 54 | DMS DMDS, PrSH | 20.83 | DMDS | 0.70 |

DMS = dimethyl sulfide,
DMDS = dimethyl disulfide,
PrSH = n-propyl mercaptan

6. The method according to claim 5, wherein the alcohol is a $C_{1-5}$-alcohol having a boiling point $\leq 290°$ C./1 bar (absolute pressure).

7. The method according to any claim 6, wherein the biochemically prepared organic compound is methanol, ethanol, 1,3-propanediol, 1,4-butanediol, 1-butanol, glycerol, tetrahydrofuran, furfural, lactic acid, succinic acid, malonic acid, citric acid, acetic acid, propionic acid, 3-hydroxypropionic acid, butyric acid, formic acid or gluconic acid.

8. The method according to claim 1, wherein the clay is a mineral from the serpentine-kaolin, talc-pyrophyllite, smectite, vermiculite, illite, mica, brittle mica, chlorite or sepiolite-palygorskite group or a mixture of two or more minerals from these groups.

9. The method according to claim 1, wherein the clay comprises a kaolinite, illite, illenite, pyrophyllite, celadonite, beidellite, nontrionite, hectorite, saponite, vermiculite, clinochlore, sheridanite, sudoite, cookeite, danobassite, rectorite, tosudite, corrensite, sepiolite, loughlinite, palygorskite, montmorillonite, bentonite, smectite, chlorite, glauconite, muscovite, vermiculite, talc or a mixture of two or more of these minerals as clay mineral.

10. The method according to claim 1, wherein the biochemically prepared compound comprises from 0 to 50% by weight of water.

11. The method according to claim 7, wherein the ethanol comprises a denaturant.

12. The method according to claim 1, wherein the clay is doped with such an amount of silver and/or silver compound that a content in the range from 0.1 to 20% by weight, calculated as Ag, is obtained.

13. The method according to claim 1, wherein the silver compound is a silver(I) salt.

14. The method according to claim 1, wherein the silver compound is silver oxide ($Ag_2O$), silver carbonate ($Ag_2CO_3$), silver nitrate ($AgNO_3$), silver sulfate ($Ag_2SO_4$), a silver halide (AgI, AgBr, AgCl, AgF) or silver sulfide ($Ag_2S$).

15. The method according to claim 1, wherein the biochemically prepared organic compound is brought into contact with the doped alumina at a temperature in the range from 10 to 200° C.

16. The method according to claim 1, wherein the biochemically prepared organic compound is brought into contact with the doped alumina at an absolute pressure in the range from 1 to 200 bar.

17. The method according to claim 1 for reducing the concentration of sulfur and/or sulfur-containing compounds by $\geq 90\%$ by weight (calculated as S).

18. The method according to claim 1 for reducing the concentration of sulfur and/or sulfur-containing compounds by $\geq 95\%$ by weight (calculated as S).

19. The method according to claim 1 for reducing the concentration of sulfur and/or sulfur-containing compounds by $\geq 98\%$ by weight (calculated as S).

20. The method according to claim 1 for reducing the concentration of sulfur and/or sulfur-containing compounds to <2 ppm by weight (calculated as S).

21. The method according to claim 1 for reducing the concentration of sulfur and/or sulfur-containing compounds to <1 ppm by weight (calculated as S).

22. The method according to claim 1 for reducing the concentration of sulfur and/or sulfur-containing compounds to <0.1 ppm by weight (calculated as S).

23. The method according to claim 1 carried out in the absence of hydrogen.

24. The method according to claim 1, wherein the respective organic compound is brought into contact with the doped alumina in the liquid phase.

* * * * *